United States Patent [19]
Barnes et al.

[11] Patent Number: 5,074,666
[45] Date of Patent: Dec. 24, 1991

[54] HIGH STABILITY INTERFEROMETER FOR MEASURING SMALL CHANGES IN REFRACTIVE INDEX AND MEASURING METHOD USING THE INTERFEROMETER

[75] Inventors: Thomas H. Barnes; Kiyofumi Matsuda; Naotake Ooyama, all of Tsukuba, Japan

[73] Assignees: Agency of Industrial Science & Technology; Ministry of International Trade & Industry, both of Tokyo, Japan

[21] Appl. No.: 475,391

[22] Filed: Feb. 5, 1990

[30] Foreign Application Priority Data

Feb. 6, 1989 [JP] Japan .................. 1-26998

[51] Int. Cl.⁵ .............................................. G01B 9/02
[52] U.S. Cl. ................................. 356/354; 356/361
[58] Field of Search ............... 356/361, 354, 355, 356, 356/353

[56] References Cited

U.S. PATENT DOCUMENTS 3,829,219  8/1974  Wyant ..................... 356/354
4,733,967  3/1988  Sommargren ............. 356/361

*Primary Examiner*—Samuel Turner
*Assistant Examiner*—Richard E. Kurtz, II
*Attorney, Agent, or Firm*—Oblon, Spivak, McClelland, Maier & Neustadt

[57] ABSTRACT

A high stability interferometer is capable of continuous measurement of small changes in the refractive index of a sample. The interferometer has a diffraction grating placed to be movable sideways or radially, and diffract laser light into beams which include +1, −1 and zero order beams. The diffraction grating is in the input plane of a Fourier Transform lens. The beams are brought to a focus in the output plane of the lens and are reflected back towards the lens by a mirror placed in the transform plane of the lens. The sample whose refractive index is to be measured is placed in the path of the +1 or −1 order beam, between the diffraction grating and the mirror.

16 Claims, 4 Drawing Sheets

HIGH STABILITY INTERFEROMETER FOR MEASURING SMALL CHANGES IN REFRACTIVE INDEX AND MEASURING METHOD USING THE INTERFEROMETER

BACKGROUND OF THE INVENTION

1. Field of the Invention

This invention relates to a high stability interferometer for measuring small changes in the refractive index of gaseous or liquid samples and to a measuring method using the interferometer.

2. Prior Art Statement

Refractive index measurement is used widely by production industries, such as for determining the concentration of solutions and monitoring the progress of chemical reactions. With small changes in the refractive index of samples often being indicative of major changes, there is a need for systems which are capable of providing continuous measurement of changes on refractive index in the order of $10^{-7}$ or less.

Conventionally, the refractive index is measured by determining the critical angle at which total internal reflection occurs, at an interface between the sample solution and a transparent substance (usually glass) whose refractive index is accurately known. Although this method can provide a good level of measurement precision, its implementation as a sampling or batch oriented technique makes it unsuitable for the on-line measurement of refractive index in production processes.

SUMMARY OF THE INVENTION

An object of this invention is therefore to provide a high stability interferometer which is capable of measuring changes in refractive index as small as $10^{-7}$ or less, continuously and automatically and a method for measuring the same using the interferometer.

To attain the above object, this invention provides a high stability interferometer for measuring small changes in refractive index comprising a light source which produces spatially coherent light; a movably-supported diffraction grating placed in the path of the light from the light source for producing from the light passing therethrough diffracted beams which include +1, −1 and zero order diffracted beams; the diffraction grating being placed in the input plane of a Fourier Transform lens through which at least the +1, −1 and zero order beams pass and are brought to a focus at the Fourier Transform output plane of the lens; a mirror placed in the Fourier Transform plane for reflecting back toward the diffraction grating the +1, −1 and zero order beams that have passed through the Fourier Transform lens; a spatial filter placed in front of the reflecting surface of the mirror for isolating the +1, −1 and zero order diffracted beams; wherein a sample whose refractive index is to be measured is placed in the path of the +1 order diffracted beam or −1 order diffracted beam between the diffraction grating and the mirror.

Light from the laser light source passes through a beam splitter to the diffraction grating which outputs various diffracted beams including +1, −1 and zero order diffracted beams. The spatial filter isolates +1, −1 and zero order beams from the diffracted light. The mirror reflects these three beams back to the diffraction grating, where they are recombined. At this time the sample is placed so that it intercepts the +1 or −1 diffracted beams. The light thus recombined is again diffracted by the diffraction grating into +1 and −1 order diffracted light beams which are detected by photodetectors.

When the diffraction grating is continuously or intermittently moved sideways, the intensities of the two beams of light output by the interferometer vary, the variation being a function of the position of the diffraction grating and the refractive index of the sample. Therefore, fluctuations in the refractive index of the sample can be determined by measuring the phase difference between the two output signals. If the sample cell is placed in the path of the +1 or −1 order beams and the sample to be measured is supplied continuously to the sample cell, it becomes possible to measure the refractive index continuously.

The above and other features and objects of the invention will become apparent with the following detailed description made with reference to the attached drawings.

DETAILED DESCRIPTION OF THE PREFERRED EMBODIMENTS

Figure 1:
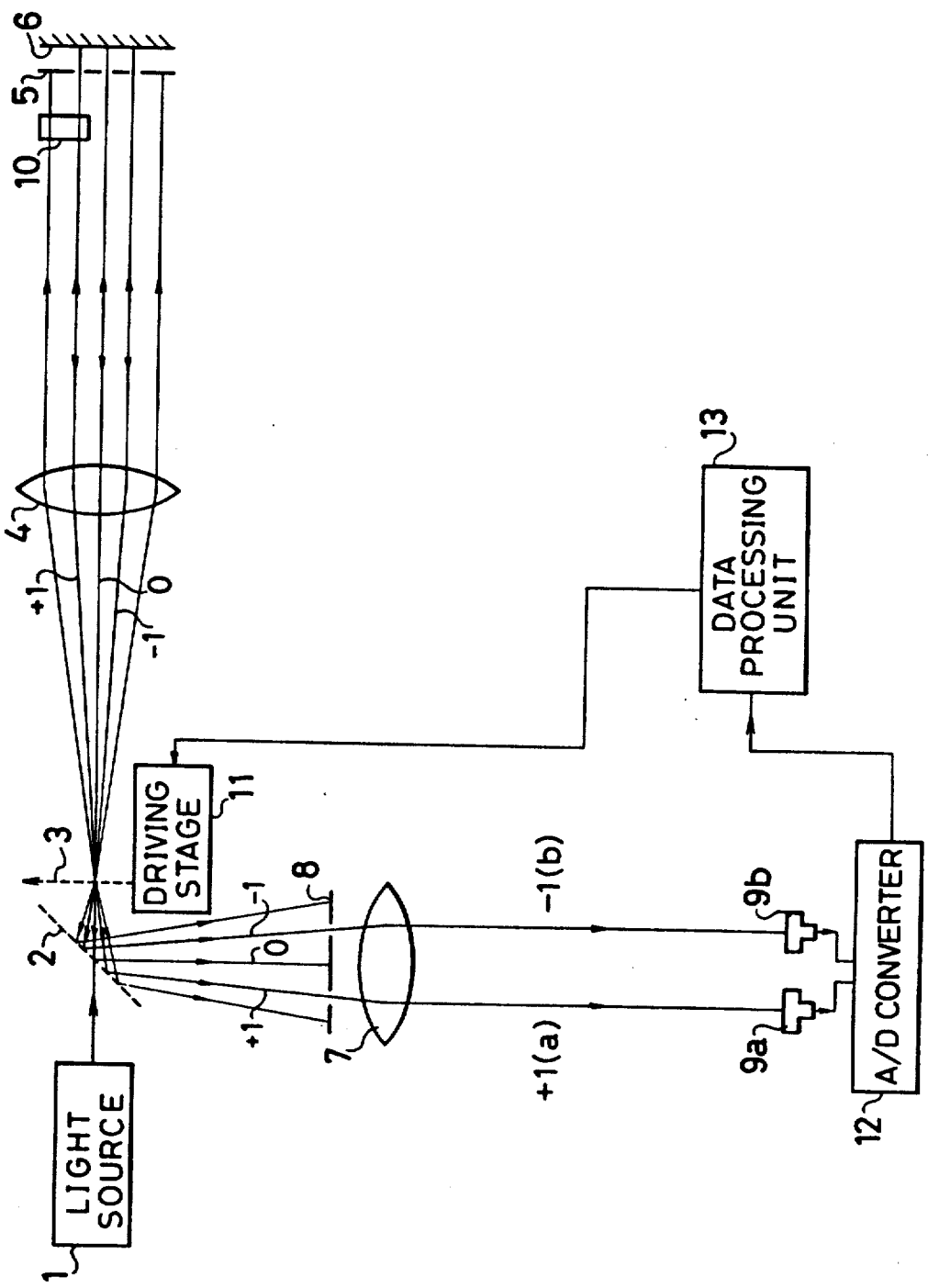
FIG. 1 is a schematic view illustrating the basic configuration of the interferometer according to the present invention.

FIG. 1 shows the basic configuration of a high stability interferometer according to this invention. With reference to the drawing, the interferometer is provided with a light source 1, a beam splitter 2, a diffraction grating 3, a Fourier Transform lens 4, a spatial filter 5 and a mirror 6, placed in that order in the path of the light from the light source 1. The interferometer is further provided with a Fourier Transform lens 7 and photodetectors 9a and 9b located on the optical axis on the light-reflection side of the beam splitter 2. A sample 10 whose refractive index is to be measured is placed in the light path between the Fourier Transform lens 4 and the spatial filter 5.

The light source 1 is, for example, a HeNe laser which emits a spatially coherent laser beam. The diffraction grating 3 may be a linear diffraction grating with a pitch of 10 lines/mm and is placed in the input plane of the Fourier Transform lens 4. The finer the pitch of the grating, the wider the angle of the diffracted light becomes. The diffraction grating 3 is supported on a driving stage 11 including a stepper motor or similar means so that the grating 3 can be moved sideways by the stage 11. The mirror 6 is placed in the output plane of the Fourier Transform lens 4, and the spatial filter 5 is placed in front of the mirror 6. The Fourier Transform lens 7 provided on the light-reflection side of the beam splitter 2 is placed so that the diffraction grating 3 is located in its input plane.

A laser beam from the light source 1 passes through the beam splitter 2 and the diffraction grating 3. Diffraction at the grating 3 divides the input laser beam into many output beams which include the $+1$, $-1$ and zero order beams $+1$, $-1$, 0. The diffraction grating 3 is placed in the input plane of the first Fourier Transform lens 4 which collimates the various diffracted beams. A portion of these beams pass through the sample 10 and impinge on the spatial filter 5, which filters out all except the $+1$, $-1$ and zero order beams. The sample 10 is positioned in the path of either the $+1$ order beam or the $-1$ order beam. In the example shown in FIG. 1, the sample 10 is in the path of the $+1$ order beam $+1$.

The three beams pass through the spatial filter 5 and are reflected by the mirror 6 back along the same respective paths, with the $+1$ order (in the illustrated example) therefore passing back through the sample 10. The three returning beams pass back through the Fourier Transform lens 4 and are recombined by diffraction at the diffraction grating 3.

The beams inclusive of the $+1$, $-1$ and zero order beams recombined by diffraction at the diffraction grating 3 described above are reflected by the beam splitter 2. The reflected beams exclusive of the $+1$ and $-1$ order beams and inclusive of the zero order beam are filtered out by the spatial filter 8, and therefore the $+1$ and $-1$ order beams $+1$, $-1$ only of the reflected beams pass through the second Fourier Transform lens 7. The focused spots of the $+1$ beam $+1$ and the $-1$ beam $-1$ appearing in the output plane of the Fourier Transform lens 7 are detected by the photodetectors 9a and 9b respectively, the output signals of which are digitized by an A/D converter 12 and sent to a DPU (data processing unit) 13.

The $+1$ and $-1$ order beams being received by the photodetectors 9a and 9b respectively are diffracted by the diffraction grating 3 so that each comprises three constituent components.

Figure 2:
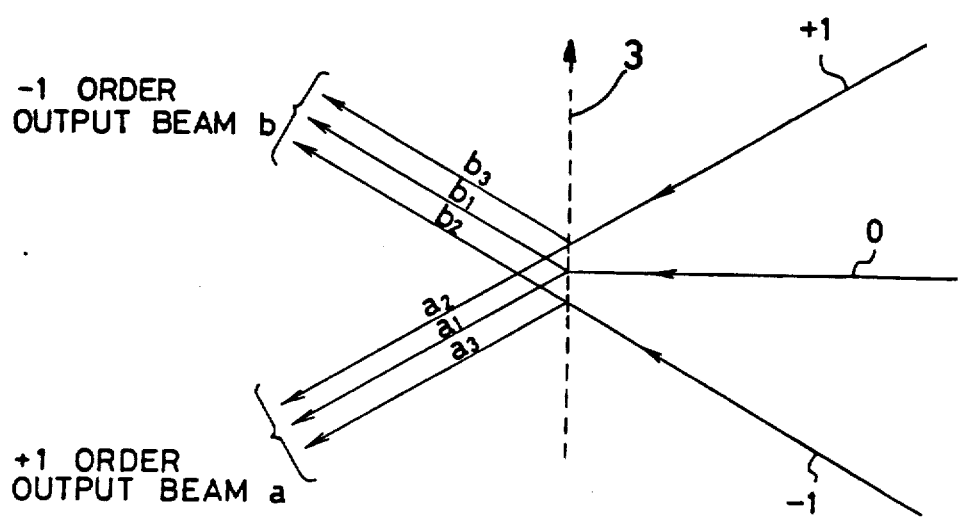
FIG. 2 is an explanatory view illustrating the configuration of diffracted beams produced by a diffraction grating of the interferometer according to this invention.

In the case of the $+1$ order output beam "a", as shown in FIG. 2, the first component $a_1$ is the zero order beam from the first diffraction at the grating 3, which is diffracted into a $+1$ output order beam on its return from the mirror 6. The second component $a_2$ is the $+1$ order beam from the first diffraction at the grating 3, which is not diffracted when it is reflected back through the grating 3 by the mirror 6. The third constituent component $a_3$ is the $-1$ order beam from the first diffraction at the grating 3, which is diffracted through two orders $(+2)$ by its reflection back through the grating 3 by the mirror 6 and therefore appears in the $+1$ output order beam "a" from the grating 3. This third component has a very small amplitude, the effect of which is to introduce an error into the phase of the intensity fluctuation of the $+1$ output beam. This error is calculated and corrected for.

The $+1$, $-1$ and zero order beams are diffracted at the same point by the diffraction grating 3, but for the sake of easy understanding they are shown in FIG. 2 as being diffracted at three different points.

Similarly, the first constituent component $b_1$ of the $-1$ order output beam "b" is the zero order beam from the first diffraction at the grating 3, which is diffracted into a $-1$ output order beam upon being reflected back by the mirror 6. The second constituent component $b_2$ is the $-1$ order beam from the first diffraction at the grating 3, which is not diffracted when it is reflected back through the grating 3 by the mirror 6 and therefore appears in the $-1$ output order beam "b". The third constituent beam component $b_3$ is the $-1$ order beam from the diffraction at the grating 3, which is diffracted through two orders $(-2)$ upon being reflected back through the grating 3 by the mirror 6, and thus appears in the $-1$ output order beam "b" from the grating 3. This third component also has a very small amplitude which introduces an error into the phase of the intensity fluctuation of the $-1$ output beam, which is calculated and corrected for.

As mentioned above, each output beam "a", "b" contains three components, two of which are strong and one of which is weak. The third component of each beam causes an error in the phase of the output beam intensity fluctuations which occur as the grating is moved sideways. This error is manifest as a non-linearity in the relationship between changes in the output phase-difference from the interferometer and changes in the refractive index of the material in the sample. It therefore gives rise to an error in the values of refractive index measured.

The shape of this non-linearity may be calculated accurately from the ratio of the intensities of the 3rd weak components $a_3$, $b_3$ in the interferometer output beams to the 1st and 2nd strong components $a_1$, $a_2$, $b_1$, and $b_2$. Before any refractive index measurements are made with the interferometer the intensities of these beams are measured and the non-linear characteristic is calculated. After that, any refractive index measurement made with the instrument (which contains errors) may therefore be corrected using the previously calculated non-linear characteristic.

When, in accordance with a signal from the DPU 13, the grating 3 may be moved sideways by a prescribed amount at a prescribed speed either continuously or intermittently by driving the driving stage 11, the phase difference between the zero order and the $+1$ order beams changes continuously and the intensities of the two output beams detected by the photodetectors 9a and 9b change periodically. In the case where the grating 3 is moved continuously, the fluctuations in the intensities of the beams detected by the photodetectors 9a and 9b are shown by graphs in FIGS. 3(a) and 3(b), respectively. When the grating 3 is moved step by step, the fluctuations in the intensities of the beams detected by the photodetectors 9a and 9b are shown by graphs in FIGS. 4(a) and 4(b), respectively, and the intensities from the photodetectors may be recorded in the DPU 13 to give data in which the intensity fluctuations are manifested as a function of the grating position to produce output signals.

As the phase difference between the constituent components making up the $+1$ order output beam is also dependent on the path difference through the sample, the phase of the intensity fluctuations in this output beam depends on the refractive index of the sample. Therefore, the refractive index variations of the sample may be determined by measuring the phase difference $\Delta f$ between the two output signals as shown in FIGS. 3 and 4. In FIG. 3(b), $w_1$ is the period of this intensity fluctuation and in FIG. 4(b), $w_2$ is the spatial period of this intensity fluctuation and $w_3$ is the size of the steps by which the grating is moved.

The DPU 13 may work in any one of several different ways, one of which is the mode of operation described below. When the grating is moved sideways by the prescribed amount by the driving stage 11, the output voltage from each photodetector 9a, 9b is measured and stored in the DPU 13. These data series oscillate at a known fundamental frequency which is fixed by the grating line spacing and the movement step size, and the phase difference between the oscillations from the two photodetectors 9a, 9b is proportional to the refractive index of the sample 10. The data series are therefore Fourier transformed by the DPU 13 and the phase of the fundamental frequency in the Fourier Spectrum calculated from the Real and Imaginary parts of the Fourier Transform. The phase difference between the detector signals is obtained simply by subtracting the phases obtained from the two Fourier Transforms.

Figure 3A:
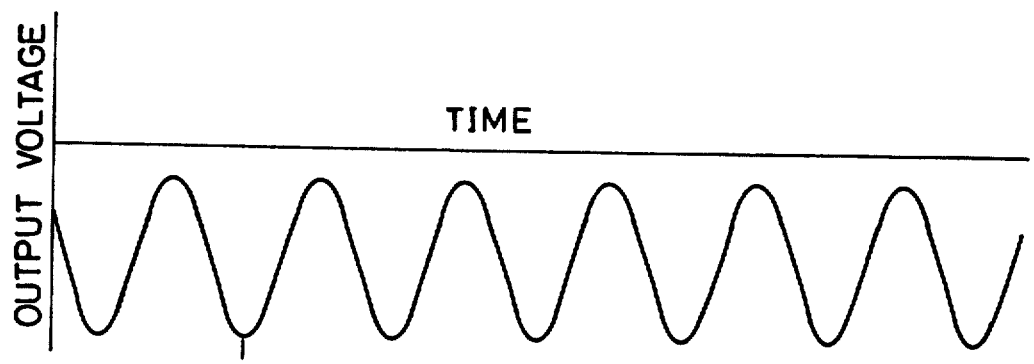
FIG. 3(a) is a graph illustrating an example waveform of the output of a first photodetector obtained when the diffraction grating is continuously moved.
Figure 3B:
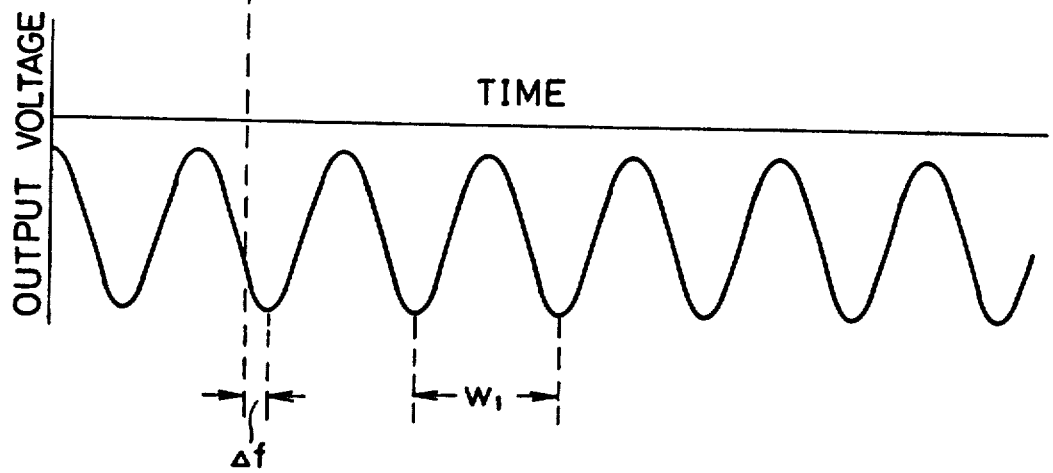
FIG. 3(b) is a graph illustrating an example waveform of the output of a second photodetector obtained when the diffraction grating is continuously moved.
Figure 4A:
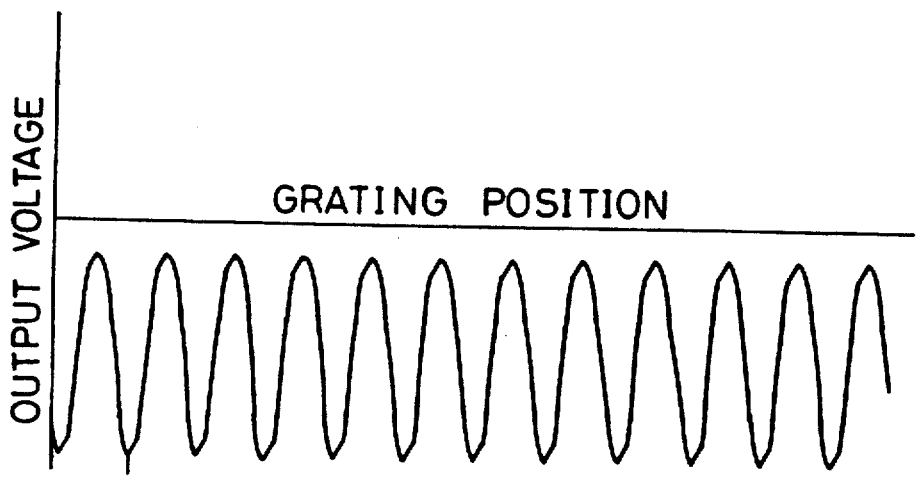
FIG. 4(a) is a graph illustrating an example waveform of the output of the first photodetector obtained when the diffraction grating is intermittently moved.
Figure 4B:
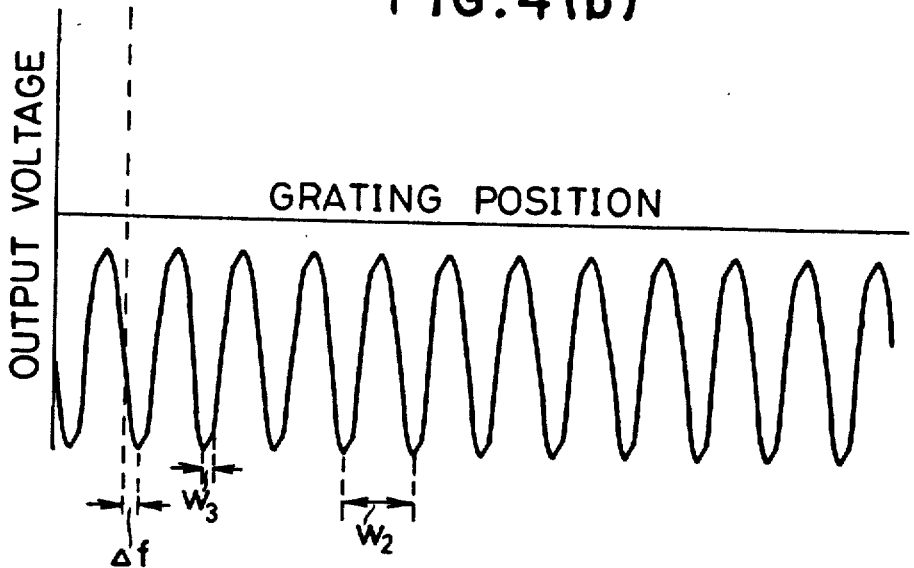
FIG. 4(b) is a graph illustrating an example waveform of the output of the second photodetector obtained when the diffraction grating is intermittently moved.

The graphs of FIGS. 3(a) and 3(b) are obtained by using a grating having a line space of 0.1 mm and continuously moving the grating by 0.6 mm. The graphs of FIGS. 4(a) and 4(b) are obtained by using a grating having a line space of 0.1 mm and moving step by step the grating by 10 μm 60 times (i.e. by 0.6 mm in total) and, in these graphs, one step movement of the grating correspond to the linear portion ($w_3$) close to the peak and the movement from one peak to the adjacent peak ($w_2$) corresponds to the movement of the grating by 50 μm (5 steps).

The refractive index of a sample can be readily measured on a continuous basis by positioning the sample cell in the light path and providing a continuous flow of the sample through the cell. In this case, the inclusion of error produced by the introduction of variations in the refractive index of the cell itself can be prevented by positioning an identical but empty cell in the path of each of the other two beams.

Assume for this example that the interferometer uses light of wavelength 632.8 nm (HeNe laser light) and the path length through the sample is 10 mm (one pass). The light passes through the sample twice. Then, if the phase difference between the detector output signals changes by, for example, 0.1 radian, the change in refractive index (RI) is given by:

$$RI \text{ Change} = \frac{0.1 \times 0.6328}{2\pi \times 2 \times 10}$$

where $\pi = 3.1415926$.

Because the interferometer uses a grating as beam splitter and recombiner, and because the sample and reference beams are close together and reflected by the same mirror 6, the instrument is extremely stable. Experiments have shown that the noise and drift are so small that, with a sample 20 mm thick and using light of wavelength 600 nm, it is possible to measure refractive index variations of the order of $0.15 \times 10^{-7}$.

Figure 5:
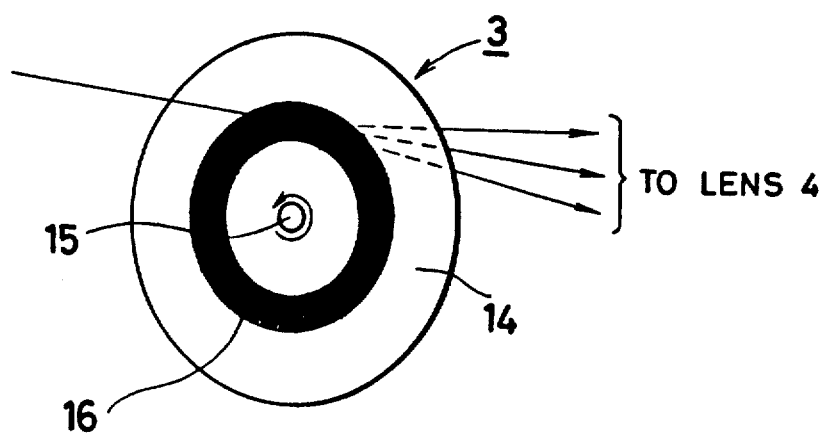
FIG. 5 is a schematic perspective view illustrating a radial diffraction grating usable for the interferometer according to this invention.

In the embodiment described above, a linear diffraction grating is used and moved sideways on the stage 11 by a stepper motor. However, it is also possible to use a radial diffraction grating 3 which comprises a transparent disk 14 forming grating lines 16 annularly with a rotary shaft 15 as the center as illustrated in FIG. 5. This radial grating 3 is rotated about its center to produce the necessary sideways translation of the lines, and hence the phase difference between the diffracted beams.

Again, although in the above embodiment the output signals from the photodetectors are analyzed by a data processing unit (i.e. a computer), if the grating moves at a constant speed, it is also possible to use a conventional phase meter to determine the phase difference between the output signals from the two photodetectors.

The instrument can be used to measure refractive index continuously if a radial grating which is rotated is used. With a radial grating, the detectors give electric output signals as long as the grating is rotating continuously, and the phase difference between these output signals is proportional to the refractive index of the sample. If a continuously rotating radial grating is used, the "step-and-sample" method of recording the photo-detector signals (as described above) is not satisfactory. In this case, the detector signals should be fed directly to an electronic phase meter. These phase meters give a direct, continuous, electronic readout of the phase difference between two electric signals connected to their inputs.

Thus, as explained above, the interferometer according to this invention is capable of measuring the refractive index of a sample continuously and automatically. The interferometer uses a grating as a beam splitter and recombiner. The $+1$, $-1$ and zero order beams from the grating are used in the interferometer and the phase difference between the $+1$ and $-1$ diffracted orders is measured.

In a conventional interferometer the phase difference between the two beams of interest is determined by combining the beams directly and examining the interference effects between them. In the interferometer of this invention, however, the $+1$ and $-1$ beams (the beams of interest) are each separately combined with the zero order beam. Thus the zero order beams acts as a common reference for the two beams of interest, and the relative interference effects from these two combinations are examined. Since the zero order beam and the $+1$ and $-1$ order beams traverse almost the same path through the interferometer, the use of the zero order beam as a common reference virtually eliminates drift arising from thermal expansion of the interferometer, variations in the wavelength of the laser and other such factors. The interferometer is therefore highly stable.

Another advantage of using the grating as a beam splitter and recombiner is that, if it is moved sideways, the relative optical frequencies of the interfering beams change, which gives rise to fluctuations in the intensities of the output beams from the interferometer which are dependent on the position of the grating and on the length of the optical path through the sample, the refractive index of which is being measured. Therefore, if the grating is moved continuously the interferometer becomes a heterodyne interferometer in which changes in the refractive index of the sample appear as variations in the phase of the electric signals. This makes it possible to measure phase very precisely, so in addition to being extremely stable, the interferometer has very high resolution. In addition, the interferometer may be constructed using simple and readily available components, and is therefore relatively inexpensive to manufacture.

What is claimed is:

1. A high stability interferometer for measuring small changes in refractive index, comprising:
   a light source for producing spatially coherent light;
   a diffraction grating placed in a path of the light from said light source for diffracting the light passing through it into beams which include +1, −1 and zero order beams;

a Fourier Transform lens having an input plane and an output plane, and arranged so that said diffraction grating is in the input plane through which at least said +1, −1 and zero order beams pass and are thereby brought to a focus in the output plane;

a sample cell for holding a sample and placed in a path of the +1 or −1 order beam that has passed through said lens;

a mirror placed in the output plane of said lens for reflecting back toward said diffraction grating the beams that have passed through said lens;

photodetecting means for detecting +1 and −1 order beams reflected by said mirror and recombined with the common zero order beam at said diffraction grating; and data processing means for determining the refractive index of said sample from the phase difference between the +1 and −1 order beams detected by said photodetecting means.

2. A high stability interferometer according to claim 1, wherein said diffraction grating is a linear diffracting grating having grating lines supported thereon so as to be movable in the direction of intersecting a path of the light from said light source.

3. A high stability interferometer according to claim 1, wherein said diffraction grating is a rotatable radial diffraction grating having grating lines supported thereon in the direction of intersecting a path of the light from said light source.

4. A high stability interferometer for measuring small changes in refractive index, comprising:

a light source for producing spatially coherent light;

a diffraction grating provided with grating lines and placed in a path of the light from said light source for diffracting the light passing through it into beams which include +1, −1 and zero order beams;

means for moving said diffraction grating in a direction for causing said grating lines to intersect a path of the light from said light source;

a first Fourier Transform lens having a first input plane and a first output plane, and arranged so that said diffraction grating is in the first input plane through which at least said +1, −1 and zero order beams pass and are thereby brought to a focus in the first output plane;

a sample cell provided with means for continuously supplying a sample to said sample cell and placed in a path of the +1 or −1 order beam that has passed through said lens;

a mirror placed in the first output plane of said first lens for reflecting back toward said diffraction grating the beams that have passed through said first lens;

a second Fourier Transform lens having a second input plane and a second output plane, and arranged so that said diffraction grating is in the second input plane so as to bring the +1 and −1 order beams recombined with the common zero order beam at said diffraction grating to a focus in the second output plane;

photodetection means placed in the second output plane of said second lens for detecting two focused spots of the +1 and −1 order beams that have passed through said second lens; and data processing means for determining the refractive index of the sample from the phase difference between the two focused spots detected by said photodetection means;

whereby the refractive index of the sample continuously supplied to said sample cell is continuously measured from a difference in phase between the two focused spots whose intensities fluctuate with the movement of said diffraction grating.

5. A high stability interferometer according to claim 4, wherein said diffraction grating is a linear diffraction grating which is supported so as to be movable along a straight line.

6. A high stability interferometer according to claim 4, wherein said diffraction grating is a radial diffraction grating which is supported so as to be rotatable about its center.

7. A high stability interferometer according to claim 4, further comprising a spatial filter which is placed in front of said mirror for isolating the +1, −1 and zero order beams diffracted by said diffraction grating and passed through said first Fourier Transform lens.

8. A high stability interferometer according to claim 4, further comprising a beam splitter which is interposed between said light source and said diffraction grating for permitting the light from said light source to permeate therethrough but reflecting the beams recombined at said diffraction grating toward said second Fourier Transform lens.

9. A high stability interferometer according to claim 4, further comprising a second spatial filter which is placed in front of said second Fourier Transform lens for filtering out the beams inclusive of the zero order beam of the recombined beams and isolating the +1 and −1 order beams of the recombined beams.

10. A method for measuring small changes in refractive index of an object with high stability, comprising the steps of:

diffracting spatially coherent light into beams inclusive of +1, −1 and zero order beams with a diffraction grating;

causing the diffracted −1, −1 and zero order beams to be incident on a first Fourier Transform lens arranged so that the diffraction grating is in an input plane of the first lens;

causing the +1 or −1 order beam output from the first lens to pass through a sample and then bringing the beams output from the first lens to a focus in an output plane of the first lens;

causing a mirror placed in the output plane of the first lens to reflect the focused beams back toward the diffraction grating via the first lens, thereby recombining the +1 and −1 order beams with the common zero order beams at the diffraction grating;

bringing the recombined +1 and −1 order beams to a focus in an output plane of a second Fourier Transform lens arranged so that the diffraction grating is in an input plane of the second lens;

detecting two focused spots of the +1 and −1 order beams; and determining the refractive index of the sample from the phase difference between the two focused spots.

11. A method according to claim 10, further comprising the step of placing a first spatial filter in front of the mirror to thereby isolate the +1, −1 and zero order beams output from the first lens and allow the isolated beams to be incident on the mirror.

12. A method according to claim 10, further comprising the step of placing a second spatial filter in an output plane of the diffraction grating at which the +1, −1 and zero beams are recombined to thereby isolate the +1 and −1 order beams of the recombined beams and allow the isolated beams to be incident on the second Fourier Transform lens.

13. A method according to claim 10, further comprising the step of moving the diffraction grating so that grating lines thereof intersect a path of the light to determine the refractive index of the sample continuously supplied to the path from a difference in phase between intensity fluctuations of the focused spots of the +1 and −1 order beams focused in the output plane of the second lens.

14. A method according to claim 13, wherein the diffraction grating is continuously moved.

15. A method according to claim 13, wherein the diffraction grating is intermittently moved.

16. A method according to claim 15, wherein the sample is incorporated in a cell having a given refractive index and placed in one of the paths of the +1 and −1 order beams, and further comprising the step of placing an empty cell having the same refractive index in the other of the paths of the +1 and −1 order beams.

* * * * *